(12) United States Patent
Oda

(10) Patent No.: US 7,794,087 B2
(45) Date of Patent: Sep. 14, 2010

(54) OPTOTYPE PRESENTING APPARATUS

(75) Inventor: Tatefumi Oda, Nukata-gun (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 12/385,133

(22) Filed: Mar. 31, 2009

(65) Prior Publication Data

US 2009/0244486 A1   Oct. 1, 2009

(30) Foreign Application Priority Data

Mar. 31, 2008   (JP) .............................. 2008-094359

(51) Int. Cl.
*A61B 3/02*   (2006.01)
(52) U.S. Cl. ...................................... 351/240; 351/242
(58) Field of Classification Search .......... 351/200–246
See application file for complete search history.

(56) References Cited

U.S. PATENT DOCUMENTS

| | | | |
|---|---|---|---|
| 5,331,358 A | 7/1994 | Schurle et al. | 351/232 |
| 5,485,231 A | 1/1996 | Hayashi et al. | 351/243 |
| 5,537,144 A | 7/1996 | Faris | 348/58 |
| 5,629,748 A * | 5/1997 | Hayashi et al. | 351/232 |
| 7,568,801 B2 * | 8/2009 | Inagaki et al. | 351/239 |
| 7,607,778 B2 * | 10/2009 | Oda | 351/240 |

FOREIGN PATENT DOCUMENTS

| | | |
|---|---|---|
| JP | A-7-236612 | 9/1995 |
| JP | A-2003-310552 | 11/2003 |

* cited by examiner

*Primary Examiner*—Mohammed Hasan
(74) *Attorney, Agent, or Firm*—Oliff & Berridge, PLC

(57) ABSTRACT

An optotype presenting apparatus capable of presenting an optotype having a high degree of flexibility to an examinee's eye while a production cost of the apparatus is curbed comprises a main body comprising an optotype forming unit comprising first and second displays displaying optotypes, and a beam combiner combining optical paths of the displays, the optotype forming unit adjusting, if optotype light bundles have polarizing axes, the axes, and providing, if optotype light bundles have no polarizing axis, polarizing axes to the bundles, whereby the bundles form optotypes having the perpendicular polarizing axes, and a projection optical system for projecting the light bundles onto the eye at a test distance, an optotype selecting unit, and a display control unit controlling the displays to display binocular-vision-test optotypes if they are selected, and controlling one of the displays to display a visual-acuity-test optotype if it is selected.

10 Claims, 6 Drawing Sheets

OPTOTYPE PRESENTING APPARATUS

BACKGROUND OF THE INVENTION

1. Field of the Invention

The present invention relates to an optotype presenting apparatus which presents an optotype for a test including an optotype for a visual acuity test and an optotype for a binocular vision test.

2. Description of Related Art

Conventionally, there is known an optotype presenting apparatus of an irradiation type which is arranged to optically make a light bundle of an optotype, the optotype formed by an optotype forming unit, at a given distance for a test with the use of a projection optical system such as a concave mirror and a beam splitter, and direct the light bundle to an examinee's eye (see Japanese Patent Application Unexamined Publication No. Hei07-236612). In addition, there is known an optotype presenting apparatus of a projection type which is arranged to enlarge and project an optotype formed by an optotype forming unit onto a screen which is apart at a given distance for a test (see Japanese Patent Application Unexamined Publication No. 2003-310552). In each of the conventional optotype forming units of these apparatuses, an optotype disk on which a predetermined optotype image is formed is rotated to selectively place the optotype on an optical path, whereby the desired optotype is presented to an examinee.

However, there is a problem that patterns of the optotypes which can be presented by the above-described apparatuses are limited because the optotypes which can be presented by those apparatuses are optotypes formed on the optotype disks only. There is another problem that because patterns of the optotypes differ among regions where the apparatuses are used, it is required to prepare optotype disks of different patterns. In addition, there is another problem that in order to present an optotype for a binocular vision test such as a stereoscopic vision test and a heterophoria test in which a polarizing plate is used, an exacting task of forming optotypes for a right eye and for a left eye of which polarizing axes are perpendicular to each other on an optotype disk plate is required, which is an arduous work, and causes an increase in production cost.

SUMMARY OF THE INVENTION

An object of the invention is to provide an optotype presenting apparatus which is capable of presenting an optotype having a high degree of flexibility while a production cost of the apparatus is curbed.

To achieve the objects and in accordance with the purpose of the present invention, an optotype presenting apparatus arranged to present an optotype to an examinee's eye comprises a main body which comprises an optotype forming unit comprising a first display arranged to display an optotype and a second display arranged to display an optotype and a beam combiner arranged to combine optical paths of the first display and the second display, the optotype forming unit arranged, in a case where light bundles of the optotypes from the first display and the second display have polarizing axes, to adjust the polarizing axes of the optotype light bundles and, in a case where light bundles of the optotypes from the first display and the second display have no polarizing axis, to provide polarizing axes to the optotype light bundles by using polarizing plates, whereby the optotype light bundles from the beam combiner form optotypes which have the polarizing axes perpendicular to each other, and a projection optical system arranged to project the optotype light bundles formed by the optotype forming unit onto an examinee's eye at a given distance for a test, an optotype selecting unit with which optotypes for a test including a first optotype for a visual acuity test and a second optotype for a binocular vision test using polarization can be selected, and a display control unit arranged to control display of the first display and display of the second display based on a selection signal from the optotype selecting unit, the display control unit arranged, in a case where the first optotype is selected, to control one of the first display and the second display to display the first optotype and, in a case where the second optotype is selected, to control one of the first display and the second display to display the second optotype for a left eye and control the other one to display the second optotype for a right eye.

Additional objects and advantages of the invention are set forth in the description which follows, are obvious from the description, or may be learned by practicing the invention. The objects and advantages of the invention may be realized and attained by the optotype presenting apparatus in the claims.

BRIEF DESCRIPTION OF THE DRAWINGS

The accompanying drawings, which are incorporated in and constitute a part of this specification, illustrate embodiment of the present invention and, together with the description, serve to explain the objects, advantages and principles of the invention. In the drawings.

DETAILED DESCRIPTION OF THE PREFERRED EMBODIMENTS

Figure 1A:
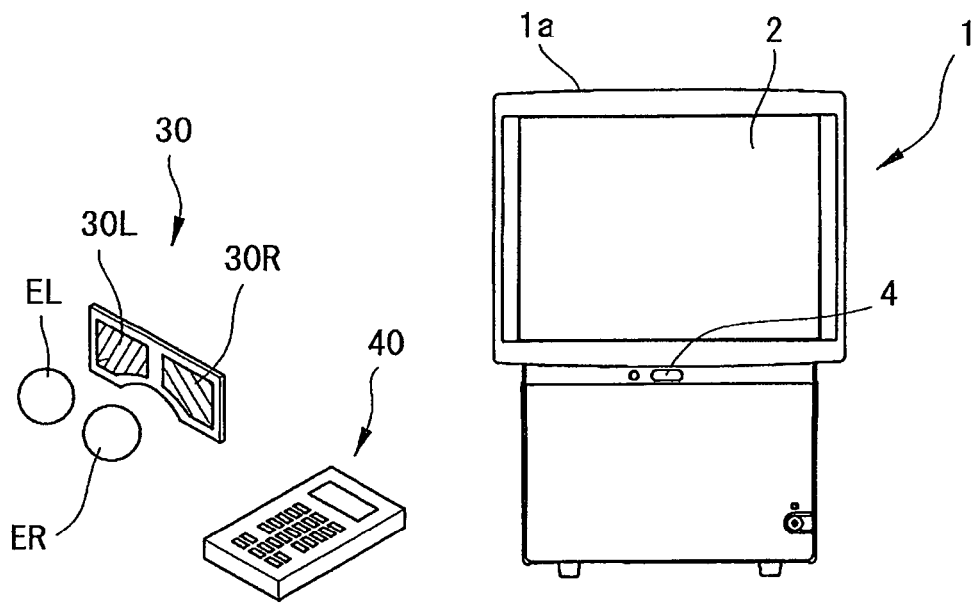
FIG. 1A is an external schematic view showing an optotype presenting apparatus according to a preferred embodiment of the present invention.
Figure 1B:
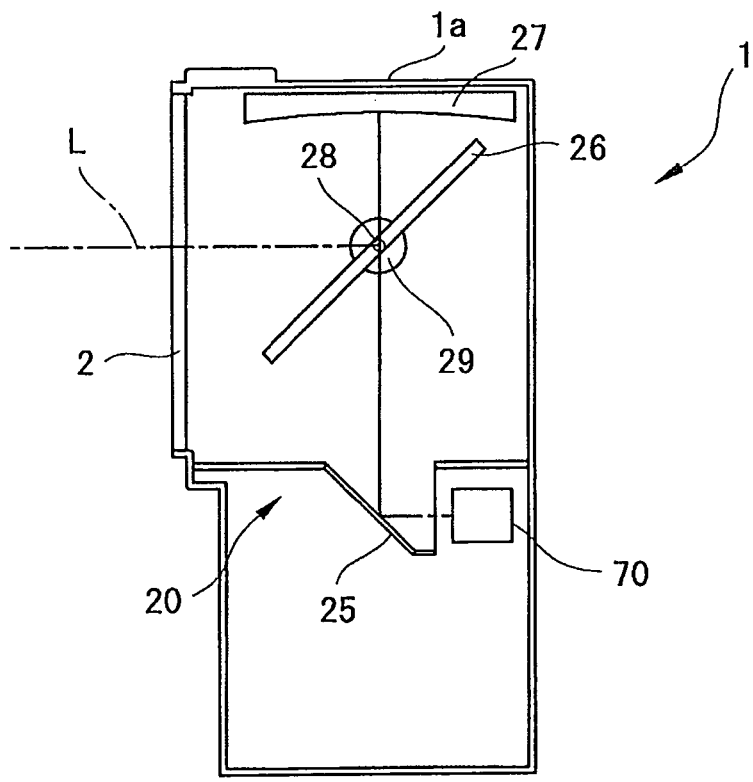
FIG. 1B is an internal structure view showing the optotype presenting apparatus viewed from the right side.

A description of one preferred embodiment of an optotype presenting apparatus embodied by the present invention will be provided below with reference to the accompanying drawings. FIGS. 1A and 1B are views showing a schematic configuration of an optotype presenting apparatus of an irradiation type according to the preferred embodiment of the present invention. FIG. 1A is an external schematic view showing the optotype presenting apparatus. FIG. 1B is a view for illustrating an internal structure of the optotype presenting apparatus, and is a perspective view showing the apparatus viewed from the right side.

A main body 1 of the optotype presenting apparatus comprises a housing 1a, and a presenting window 2 which is made of an acrylic plate on which an antireflection film is formed and is placed on a front surface of the housing 1a such that an examinee can see an optotype for a test (hereinafter, referred to simply as an optotype) which is formed inside the housing 1a through the presenting window 2. The inside of the housing 1a is painted black so that the internal structure thereof is not easy to see. A transmitting and receiving portion 4 is provided on the front surface of the housing 1a and is arranged to transmit and receive a light signal from and to a remote control 40 that defines an optotype selecting mechanism to be described later.

It is arranged that if the optotype presented by the optotype presenting apparatus is an optotype for a binocular vision test using polarization, polarization spectacles 30 comprising a polarizing plate 30L and a polarizing plate 30R of which polarizing axes are perpendicular to each other are placed in front of right and left eyes (ER and EL) of the examinee. In the polarization spectacles 30 which are used in the field of ophthalmology, the polarizing plate 30L for a left eye has the polarizing axis oriented in the direction of 45 degrees, and the polarizing plate 30R for a right eye has the polarizing axis oriented in the direction of 135 degrees. Also in using a subjective eye refractive power measurement apparatus in which corrective lenses such as spherical lenses are switched to be placed in right and left test windows in order to perform subjective examination for refractive power correction, it is arranged that a polarizing plate having a polarizing axis oriented in the direction of 45 degrees and a polarizing plate having a polarizing axis oriented in the direction of 135 degrees are placed in front of the left test window and the right test window, respectively.

Next, a description of an optical system placed inside the housing 1a will be provided. Inside the housing 1a, an optotype forming unit 70 arranged to form an optotype for a test, and a projection optical system 20 arranged to direct a light bundle of the optotype formed by the optotype forming unit 70 to the examinee's eye are provided. The projection optical system 20 comprises a mirror 25, a beam splitter 26 and a concave mirror 27. The concave mirror 27 used in the preferred embodiment of the present invention is designed to have a focal length such that an optical distance between the optotype and the examinee's eye becomes a distance for a test of 5 m when the distance between the examinee' eye and the presenting window 2 of the housing 1a is 1.1 m.

The light bundle of the optotype formed by the optotype forming unit 70 is reflected upward by the mirror 25, is transmitted by the beam splitter 26, and is reflected by the concave mirror 27. The optotype light bundle reflected by the concave mirror 27 is reflected by the beam splitter 26 to be directed to the examinee's eye through the presenting window 2. The projection optical system 20 is arranged to present a virtual image to the examinee's eye, which is obtained by magnifying the optotype formed by the optotype forming unit 70 by about 5 to 20 times (13 times in the preferred embodiment of the present invention). In other words, the projection optical system 20 defines an optical system by which the optotype formed by the optotype forming unit 70 and the examinee's eye are placed optically apart from each other at a predetermined distance for a test.

The beam splitter 26 is placed obliquely on an optical axis L of the concave mirror 27 and is arranged to be rotated by a rotary motor 29 in a vertical (up/down) direction about a rotation shaft 28 extending in a horizontal direction on the optical axis L. The rotation of the beam splitter 26 changes the height of the optotype light bundle which is reflected by the beam splitter 26 to be directed to the examinee's eye according to the height of the examinee's eye.

Figure 2A:
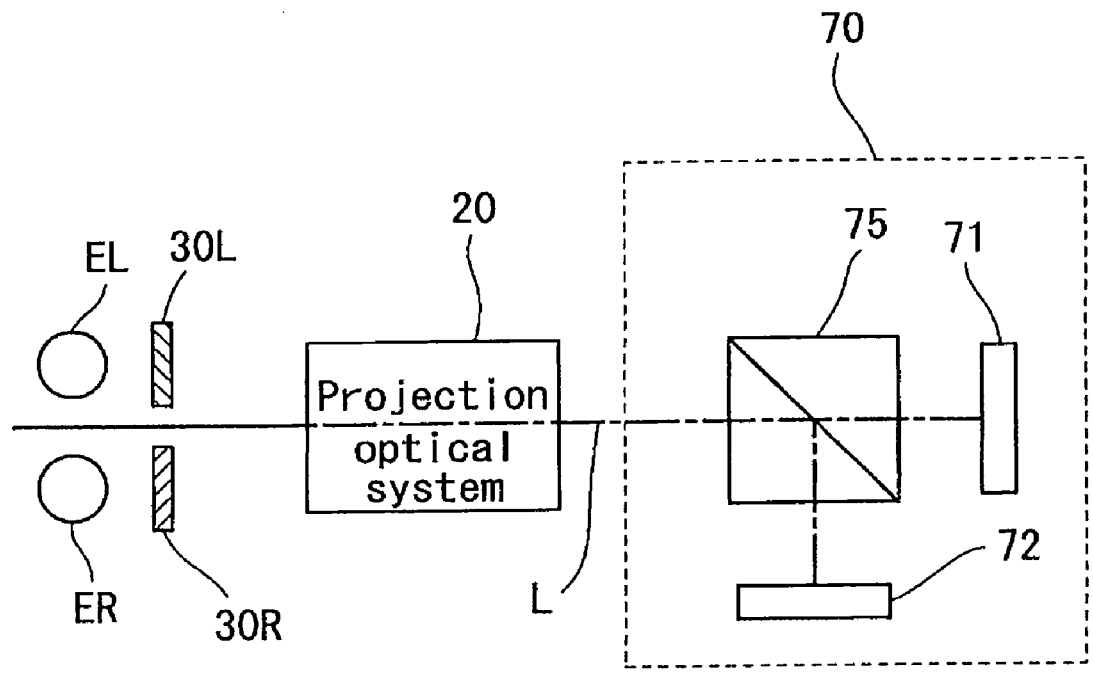
FIG. 2A is a diagram showing a configuration of an optotype forming unit.

FIG. 2A is a diagram showing a configuration of the optotype forming unit 70. The optotype forming unit 70 comprises a first display (an LCD 71) and a second display (an LCD 72) each arranged to display an optotype for a test including an optotype for a binocular vision test (a second optotype) and an optotype for a visual acuity test (a first optotype). The optotype forming unit 70 further comprises a polarization beam combiner 75 having a property of transmitting a light bundle which has a predetermined polarization direction (a polarizing axis oriented in a predetermined direction) and reflecting a light bundle which has a polarization direction (a polarizing axis) perpendicular to the transmitted light bundle, the polarization beam combiner 75 arranged to combine light bundles of the optotypes from the two displays (the LCDs 71 and 72) on the optical axis L of the projection optical system 20. The optotype forming unit 70 is arranged such that in a binocular vision test in which different optotypes are presented to right and left eyes by using polarization, the optotype for a right eye and the optotype for a left eye are displayed respectively on the second display (the LCD 72) and the first display (the LCD 71), and the combination of the optotype light bundles from both the displays by the polarization beam combiner 75 forms an optotype for a binocular vision test. In addition, the optotype forming unit 70 is arranged such that when an optotype for a test such as a binocular vision test other than the binocular vision test using polarization (e.g., a red-green test) and a visual acuity test is presented, the optotype is displayed on either one of the first display and the second display.

In the preferred embodiment of the present invention, color liquid crystal displays (the LCDs 71 and 72) of the same characteristics (e.g., a polarization direction, light emission intensity, a resolution) and of the same size are used for the first display and the second display. The color liquid crystal displays of the LCDs 71 and 72 each comprise a backlight, a first polarizing plate, a liquid crystal section, a color filter and a second polarizing plate of which a polarizing axis is perpendicular to that of the first polarizing plate, which are arranged in this order from behind. The LCDs 71 and 72 are each preferably arranged such that linear polarized light emitted from the second polarizing plate has a polarization direction (a polarization angle) of the same angle as the polarizing axis of either one of the polarizing plates 30R and 30L which are placed in front of the examinee's right and left eyes. For example, the LCDs 71 and 72 emit linear polarized light oriented in the direction of 45 degrees. The polarization direction of the light emitted from each of the LCDs 71 and 72 is defined with respect to a horizontal direction of a square-shaped display screen (a surface where an optotype is to be displayed). The LCDs 71 and 72 are shaped square, and accordingly have square-shaped display regions.

In addition, the first and second displays (the LCDs 71 and 72) used in the preferred embodiment of the present invention are each arranged such that pixels (resolution) thereof are determined so as to satisfy conditions that an optotype for visual acuity of 2.0 (VA 2.0) which is the smallest optotype among optotypes for a visual acuity test can be presented by the main body 1, and that the optotypes displayed on the LCDs 71 and 72 (the optotypes formed by the optotype forming unit 70) can be magnified (by 5 to 20 times in this condition) by the projection optical system 20 and presented to the examinee's eye.

In a Landort-ring optotype for visual acuity of 2.0, which is used as the optotype for a visual acuity test, the width of a gap of the optotype is 0.5 minute (1/120 degree) of visual angle. Assuming that the test distance is 5 m, the width of the gap of the Landort-ring optotype is about 727 μm. By dividing the width by the magnification of the projection optical system 20, the width of a gap of a Landort-ring optotype to be displayed on a display (an LCD) is obtained. Assuming that the magnification is 13 times, the widths of the gaps of the Landort-ring optotypes displayed on the LCDs 71 and 72 become 56 μm.

Therefore, for the LCDs 71 and 72, liquid crystal displays each arranged to have the pixels of 56 μm square or less are used. The pixels of the LCDs 71 and 72 are preferably one-half of or less than one-half of the width of the gap of the Landort-ring optotype for visual acuity of 2.0 (e.g., 28 μm), and more preferably one third of or less than one third of the width (e.g., 19 μm). Thus, the Landort-ring optotype for visual acuity of 2.0 can be displayed smoothly preferably through smoothing process.

In addition, the displays (the LCDs 71 and 72) are each arranged such that the size thereof is determined so as to satisfy a condition that an optotype for visual acuity of 0.03 which is the largest optotype among the optotypes for a visual acuity test can be presented by the main body 1. In a Landort-ring optotype for visual acuity of 0.03, which is used as the optotype for a visual acuity test, the width of a gap of the Landort-ring optotype is 50 mm at the test distance of 5 m. This is because the width of the gap of the optotype is about 33.3 minutes of visual angle. Accordingly, the widths of the gaps of the Landort-ring optotypes displayed on the LCDs 71 and 72 become 3.8 mm, and the entire lengths of the Landort-ring optotypes become about 19 mm (this is because the entire length of a Landort-ring optotype is 5 times as long as the width of its gap). Therefore, it is preferable that the LCDs 71 and 72 each have the size of at least 19 mm square, and it is more preferable that the LCDs 71 and 72 each have the size of 20 to 24 mm square if a background of a test region of each of the optotypes is taken into consideration.

As described above, the pixels and the size of the displays (the LCDs 71 and 72) are determined while those conditions such as the pixels and the size of the displays are not limited to the above-described conditions and are determined as appropriate according to the magnification of the projection optical system or the upper and lower limits of visual acuities of the optotypes for a visual acuity test which can be presented.

In a practical use, the LCDs 71 and 72 are fixed to the cube polarization beam combiner 75 while they are shown for the sake of illustration in FIG. 2A such that spaces are provided between the LCDs 71 and 72 and the polarization beam combiner 75.

Next, descriptions of a positional relation between the LCDs 71 and 72, and combination of the optotypes will be provided. The positional relation between the LCDs 71 and 72 is schematically shown in FIG. 2A, and the polarization directions of the LCDs 71 and 72 are schematically indicated with the broken lines in FIG. 2B.

Figure 2B:
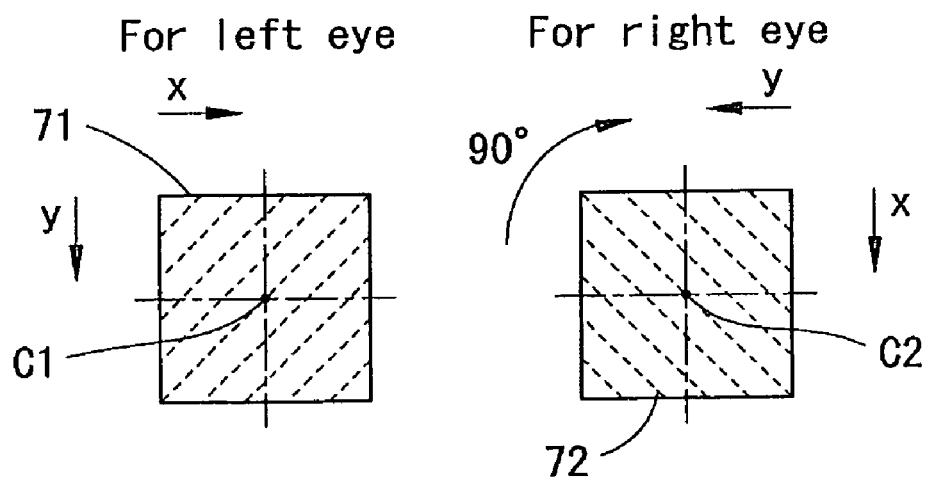
FIG. 2B is a view showing a relation of a display screen of a first display to a display screen of a second display.

The polarization beam combiner 75 is arranged to transmit the light bundle from the LCD 71 which has a polarization direction of 45 degrees, and reflect the light bundle from the LCD 72 which has a polarization direction of 135 degrees which is perpendicular to the polarization direction of 45 degrees. Since the LCDs of the same type are used for the LCDs 71 and 72, the LCDs 71 and 72 are positioned so as to have a relation such that the display screen of the LCD 72 is rotated 90 degrees with respect to the display screen of the LCD 71 in order to make the polarization directions of the light bundles from the LCDs 71 and 72 perpendicular to each other (see FIG. 2B). Consequently, the polarization direction of the light bundle from the LCD 72 is made 135 degrees. In addition, the LCDs 71 and 72 are fixed to the polarization beam combiner 75 and are positioned such that a center line C1 (a pixel in the center of the display region) of the LCD 71 and a center line C2 (a pixel in the center of the display region) of the LCD 72 shown in FIG. 2B are combined coaxially on the optical axis L of the projection optical system 20 and become the center of the optotype for a binocular vision test.

In fixing the LCDs 71 and 72 to the polarization beam combiner 75, alignment of the center lines C1 and C2 is performed in order to make each of the center lines C1 and C2 coaxial with the optical axis L1; however, since fine positional adjustment of the LCDs 71 and 72 is difficult to perform in consideration of pixels, the alignment (fine positional adjustment) is performed through electronic processing to be described below. That is, because each of the LCDs 71 and 72 is a display where a plurality of given pixels are arranged in a matrix and display addresses are assigned to the pixels, by storing in a memory 11 (to be described) in advance a mutual relation between the display addresses of the pixels in the LCDs 71 and 72 to be combined coaxially by the polarization beam combiner 75, electronic alignment of the center lines C1 and C2 is performed. To be specific, it is preferable that if the display address corresponding to the center line C1 of the LCD 71 is (s, t), the display address corresponding to the center line C2 of the LCD 72 (the display address in a state where the LCD 72 is rotated 90 degrees with respect to the LCD 71) is (s, t). If the display address corresponding to the center line C1 of the LCD 71 is displaced upward by one pixel (in coordinates on the LCD 71) (i.e., if the display address is displaced in a Y-direction by one pixel), the display address of the center line C2 of the LCD 72 is adjusted so as to be (s, t−1). Information on the mutual relation between the display addresses is adjusted for each apparatus and is stored in the memory 11. A control unit 10 to be described is arranged to control, based on the adjusted information on the mutual relation between the display addresses stored in the memory 11, the LCD 71 and the LCD 72 to display the optotype for a left eye and the optotype for a right eye which are to form the optotype for a binocular vision test by using the polarized light so as to have a given relation. Accordingly, even if there is a manufacturing error in the optotype forming unit 70 which is caused during the production process thereof, the fine positional adjustment of the optotype for a left eye and the optotype for a right eye which are to form the optotype for a binocular vision test is performed with ease.

Because the LCDs 71 and 72 are placed so as to have the positional relation that the LCD 72 is rotated 90 degrees with respect to the LCD 71, the display of the LCD 71 and the display of the LCD 72 are controlled by the control unit 10 such that the optotype for a left eye displayed on the LCD 71 and the optotype for a right eye displayed on the LCD 72 have a relation that the optotype for a right eye displayed on the LCD 72 is rotated 90 degrees with respect to the optotype for a left eye displayed on the LCD 71. In other words, the display of the optotypes is controlled taking it into account that rows (x) and columns (y) of the display addresses (x, y) of the pixels in the LCD 72 are rotated 90 degrees with respect to rows (x) and columns (y) of the display addresses (x, y) of the pixels in the LCD 71. Further, the LCD 72 which is placed on an optical path reflected by the polarization beam combiner 75 is arranged such that the display addresses (x, y) of the optotype for a right eye are controlled in accordance with mirror inversion which is made by the polarization beam combiner 75.

Almost all of the light bundle of the optotype for a right eye which is displayed on the LCD 72 is reflected by the polarization beam combiner 75. Meanwhile, almost all of the light bundle of the optotype for a left eye which is displayed on the LCD 71 is transmitted by the polarization beam combiner 75. Hence, the light bundles from the LCDs 71 and 72 (having the center lines C1 and C2 as their centers, respectively) are combined on the optical path L of the projection optical system 20, and the optotype (e.g., an optotype for a binocular vision test) is formed by the optotype forming unit 70 and is presented to the examinee through the projection optical system 20. The combining of the light bundles of the optotypes which are displayed on the LCDs 71 and 72 allows losses of light intensity in each of the LCDs 71 and 72 to be minimized or prevented, and allows the optotype light bundles from the optotype forming unit 70 to be directed to the projection optical system 20. This is because the polarization beam combiner 75 has the property of total transmission and total reflection according to the polarization direction, and because almost all of the light bundles from the LCDs 71 and 72 reach the optical axis L.

Test regions of the optotypes displayed on the LCDs 71 and 72 (i.e., white background regions in displaying black optotypes for a visual acuity test) are defined by the sides of the display regions of the respective LCDs 71 and 72. Accordingly, each of the whole surfaces of the display regions of the LCDs 71 and 72 becomes a display surface for displaying an optotype, and the test regions are shaped square in the preferred embodiment of the present invention. Besides, application of a mask or other items in displaying an optotype may scale down the test regions.

Figure 3:
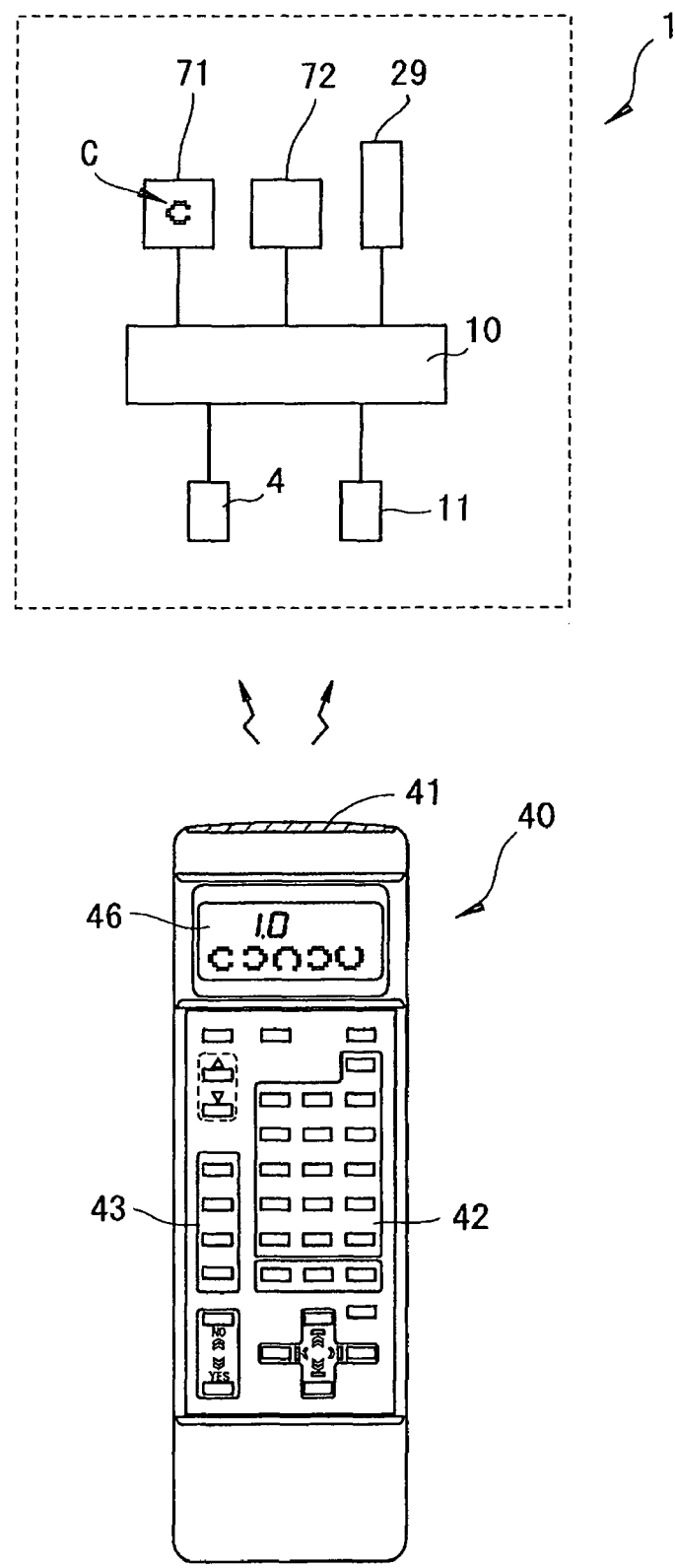
FIG. 3 provides a control block diagram of the optotype presenting apparatus and a configuration diagram of a remote control.

FIG. 3 provides a control block diagram of the main body 1 and a configuration diagram of the remote control 40. The optotype to be presented to the examinee is selected (switched) with the use of the remote control 40. The remote control 40 that defines the optotype selecting mechanism (the optotype selecting unit) comprises switches 42 with which an optotype for a visual acuity test is selected for performing a visual acuity test on the examinee's eye, switches 43 with which an optotype for a binocular vision test is selected for testing binocular visual performance of the examinee's eyes, and a display 46 arranged to display the selected optotype, information on the control of the remote control 40 and other information. A communication window 41 is provided on a front portion of the side of the remote control 40, through which a signal for controlling the main body 1 is sent to the main body 1 and a signal from the main body 1 is received.

Next, the operation of the apparatus having the above-described structure in performing a test will be described. The examinee is placed at the predetermined position of 1.1 m away from the presenting window 2 of the housing 1a, whereby the test distance is set to be the predetermined optical distance (5 m). An optotype selection signal generated by the operation of the remote control 40 is sent to the main body 1 through the communication window 41, and the signal received by the transmitting and receiving portion 4 is sent to the control unit 10. Based on the signal fed through the transmitting and receiving portion 4, the control unit 10 refers, in order to present the selected optotype through the presenting window 2, to the information in the memory 11 which is connected to the control unit 10 and stores optotype patterns and other information, and controls the LCDs 71 and 72 to display the selected optotype. The degree of flexibility of the optotype to be displayed on the LCDs 71 and 72 can be increased by storing optotype patterns of various types in the memory 11 in advance. Change or addition to the optotype patterns can be easily made, if desired, by rewriting the stored data in the memory 11. When a given switch of the remote control 40 is operated in the vicinity of the examinee's eye, the control unit 10 drives the motor 29 to change and adjust the angle in the vertical (up/down) direction of the beam splitter 26, and thereby the optotype light bundle is directed to the height of the examinee's eye, a detailed description of which is omitted.

When an optotype for a visual acuity test is selected with the use of the switches 42, a Landort-ring optotype C for given visual acuity (see FIG. 3), for example, is displayed on the LCD 71 (or the LCD 72), while the LCD 72 (or the LCD 71) is not driven and no optotype is displayed thereon. This is because the optotype for a visual acuity test is satisfactorily formed by using only one of the two LCDs 71 and 72. Hence, the optotype light bundle directed to the examinee's eye by the projection optical system 20 is only the light emitted from the LCD 71 (or the LCD 72). In addition, since the polarization direction of the linear polarized light emitted from the LCD 71 coincides with the polarization direction of the light bundle which the polarization beam combiner 75 transmits, losses of light intensity can be minimized or prevented, which brings an advantage over the use of a half mirror (i.e., a high-luminance LCD is not required and accordingly the production cost is curbed). In addition, using only one of the LCDs can save power consumption of the apparatus. Further, if the two LCDs are arranged to alternately display an optotype for a visual acuity test at given time intervals, it is possible to get more life out of the two LCDs.

Further, the following advantages are brought. That is, while high-precision alignment of the center lines C1 and C2 of the LCDs 71 and 72 is required in order to achieve proper presentation of the optotypes to the examinee in a case where the same optotypes for a visual acuity test are presented on the LCDs 71 and 72, especially in a case where small (fine) optotypes for visual acuity of 2.0 are presented on the LCDs 71 and 72, such high precision alignment is not necessarily required in a case where the optotype is formed on only one of the LCDs. Therefore, the display (forming) of the optotype on only one of the two LCDs allows easy production and easy adjustment of the apparatus, which curbs a production cost of the apparatus.

Used preferably as the optotypes for a visual acuity test are optotypes of letters for various visual acuity. Alternately, it is preferable that an optotype for a red-green test is formed by the optotype forming unit 70 as an optotype for a visual acuity test which does not require to be separated into an optotype for a right eye and an optotype for a left eye using polarization.

Next, the case of presenting an optotype for a binocular vision test with the use of the polarization spectacles 30 will be described. When a switch for selecting, for example, an optotype for a stereoscopic vision test is selected among the switches 43 using the remote control 40, an optotype for a binocular vision test (an optotype 60 for a stereoscopic vision test) is presented in the presenting window 2 as shown in FIGS. 4A to 4D.

Figure 4A:
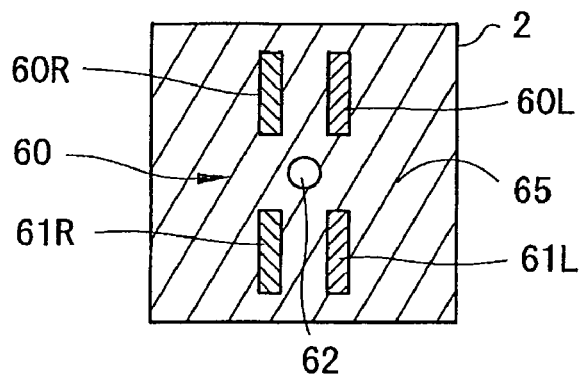
FIG. 4A is a view showing an optotype for a stereoscopic vision test presented in a presenting window in the case of being seen without using polarization spectacles.
Figure 4B:
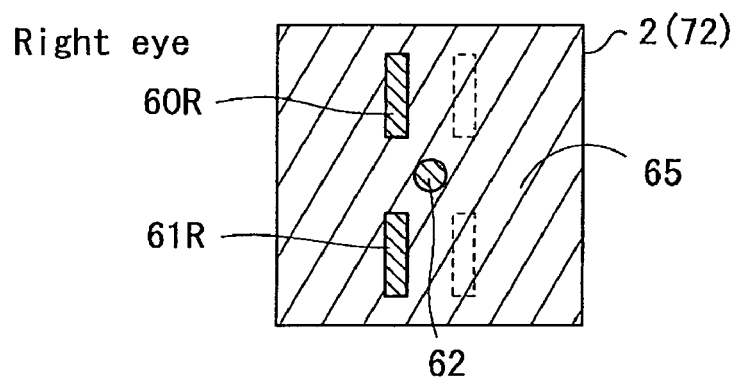
FIG. 4B is a view showing how the presenting window is seen through the polarization spectacles by a right eye.
Figure 4C:
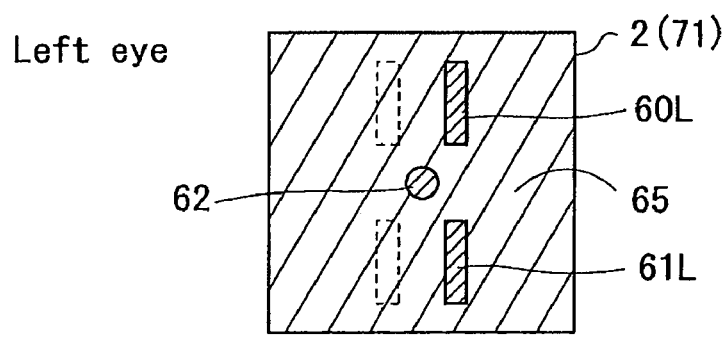
FIG. 4C is a view showing how the presenting window is seen through the polarization spectacles by a left eye.

FIG. 4A is a view of the optotype 60 for a stereoscopic vision test presented in the presenting window 2 in the case of being seen without using the polarization spectacles 30. FIGS. 4B and 4C are views showing how the presenting window 2 is seen through the polarization spectacles 30 by the right eye and the left eye, respectively. Accordingly, shown in FIG. 4B is the screen on which the optotype displayed on the LCD 72 is presented, and shown in FIG. 4C is the screen on which the optotype displayed on the LCD 71 is presented.

In FIG. 4A, a background screen 65 is black, and a fusion stimulus optotype 62 that defines a fusion stimulus for both of the eyes is white and is positioned in the center of the presenting window 2. The black background screen 65 is unaffected by polarized light. Vertically-long optotypes 60R, 61R, 60L and 61L in white (or in light blue green) are positioned above and below the fusion stimulus optotype 62. The vertically-long optotypes 60R and 61R are used to be visually perceived by the right eye and are displayed in a polarization direction of 135 degrees on the LCD 72. The vertically-long optotypes 60L and 61L are used to be visually perceived by the left eye and are displayed in a polarization direction of 45 degrees on the LCD 71. The fusion stimulus optotype 62 is displayed on both of the LCDs 72 and 71 because it needs to be visually perceived by each of the right and left eyes. The vertically-long optotype 60R for a right eye and the vertically-long optotype 60L for a left eye are displayed in the same shape, in the same size and in the same color. The distance between the optotypes 60R and 60L is set to have a desired stereoparallax (e.g., 10 minutes and 30 seconds) in relation to the test distance. The same applies to the vertically-long optotype 61R for a right eye and the vertically-long optotype 61L for a left eye.

Display addresses of the fusion stimulus optotype 62 and the vertically-long optotypes 60L and 61L which are displayed on the LCD 71, and display addresses of the fusion stimulus optotype 62 and the vertically-long optotypes 60R and 61R which are displayed on the LCD 72 are controlled by the control unit 10 based on the mutual relation between the display addresses stored in the memory 11. In addition, the display addresses of the optotypes displayed on the LCD 72 are controlled by the control unit 10 in accordance with the positional relation that the LCD 72 is rotated 90 degrees with respect to the LCD 71 and the mirror inversion made by the polarization beam combiner 75. Accordingly, when seen by both the eyes, the optotype for a right eye and the optotype for a left eye of which the optotype 60 for a stereoscopic vision test are made up are formed to have a desired positional relation as shown in FIG. 4A.

Figure 4D:
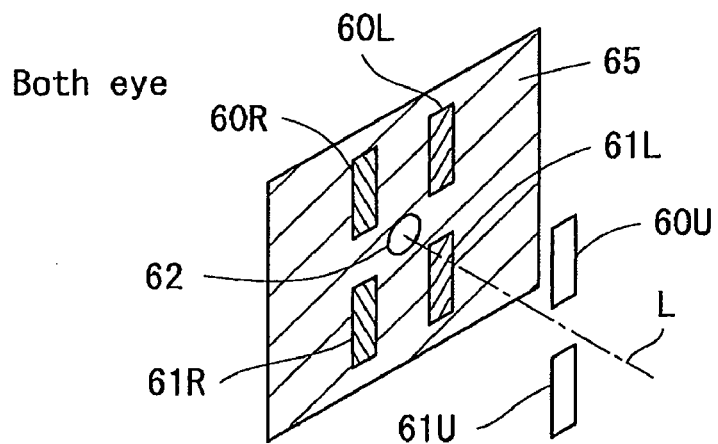
FIG. 4D is a view for illustrating how the optotype for a stereoscopic vision test is seen.

Light bundles of the vertically-long optotypes 60R and 61R and the fusion stimulus optotype 62 displayed on the LCD 72 and light bundles of the vertically-long optotypes 60L and 61L and the fusion stimulus optotype 62 displayed on the LCD 71 are combined coaxially on the optical axis L of the projection optical system 20 by the polarization beam combiner 75, and are directed to the examinee's eyes. The light bundles which have polarization directions the same as the polarizing plate 30R or the polarizing plate 30L reach the respective eyes, whereby the vertically-long optotypes 60R and 61R and the fusion stimulus optotype 62 displayed on the LCD 72 are seen by the right eye while the vertically-long optotypes 60L and 61L and the fusion stimulus optotype 62 displayed on the LCD 71 are not seen by the right eye and they seem assimilated to the black color of the background (the background screen 65). The opposite applies to the left eye. When the examinee sees the presenting window 2 by both the eyes, a fusion optotype 60U which is made up of the vertically-long optotypes 60R and 60L looks like floating with respect to the fusion stimulus optotype 62 as shown in FIG. 4D by degrees corresponding to a desired parallax. A fusion optotype 61U which is made up of the vertically-long optotypes 61R and 61L looks like floating with respect to the fusion stimulus optotype 62 in the same manner. If the polarization spectacles 30 are used reversed (i.e., if the polarizing plate having the polarizing axis oriented in the direction of 45 degrees is placed in front of the right eye and the polarizing plate having the polarizing axis oriented in the direction of 135 degrees is placed in front of the left eye), the fusion optotypes 60U and 61U look like sinking down with respect to the fusion stimulus optotype 62. In this stereoscopic vision test, slow floating is diagnosed as a tendency of exophoria, and slow sinking is diagnosed as a tendency of esophoria.

For the optotype for a binocular vision test, which requires the simultaneous use of the two LCDs 71 and 72, an optotype for a heterophoria test, an optotype for a detailed stereoscopic vision test, an optotype for a binocular balance test, and an optotype for an aniseikonia test are preferably used in addition to the optotype for a stereoscopic vision test shown in FIGS. 4A to 4D.

In the present invention, the optotype presenting apparatus comprises the displays which are each capable of forming (displaying) the optotype with flexibility. Thus, a visual acuity test with a high degree of flexibility can be performed. To be specific, rewriting the information stored in the memory 11 allows various optotypes to be easily prepared, which eliminates the need for preparing optotype disks of different patterns which differ among regions where optotype presenting apparatuses are used, the need required in conventional apparatuses, so that a production cost of the apparatus can be curbed. If memory capacity of the memory 11 is sufficiently high, it is also preferable that the apparatus is arranged such that all types of optotypes are stored in the memory 11 and changes of optotype readout setting are made according to the usage of the apparatus or the region where the apparatus is used.

In addition, the apparatus is arranged such that in the binocular vision test, the optotype for a left eye and the optotype for a right eye are formed on the respective displays (the LCDs 71 and 72) and are made to have the respective polarization directions by the polarization beam combiner 75, so that the optotypes which have the polarization directions respectively for the left eye and the right eye are easily formed. Thus, exacting tasks of attaching the polarizing plate for a right eye having the polarizing axis oriented in the direction of 135 degrees to a portion corresponding to the optotype for a right eye in the optotype for a binocular vision test on the optotype disk and attaching the polarizing plate for a left eye having the polarizing axis oriented in the direction of 45 degrees to a portion corresponding to the optotype for a left eye in the optotype for a binocular vision test on the optotype disk, which are required in conventional apparatuses, are not required in the apparatus according to the preferred embodiment of the present invention. Thus, the apparatus is readily manufactured and a production cost of the apparatus is curbed.

While the liquid crystal displays which are provided in advance with the predetermined polarization directions (i.e., provided with the polarizing plates) are used for the first and second displays in the preferred embodiment of the present invention, the present invention is not limited thereto. It is essential only that an optotype for a binocular vision test which is formed by an optotype forming unit be provided with polarization directions for right and left eyes. For example, a display having no polarized light such as an organic EL display may be used for both of the first and second displays. In this case, as having a property of a polarizing plate, the polarization beam combiner 75 provides polarization directions respectively to light bundles of optotypes from the displays, whereby an optotype for a binocular vision test is formed in a similar manner to the above-described optotype forming unit 70. In this case, it is not necessary that the organic EL displays have a positional relation that one of the organic EL displays is rotated 90 degrees with respect to the other organic EL display.

Figure 5:
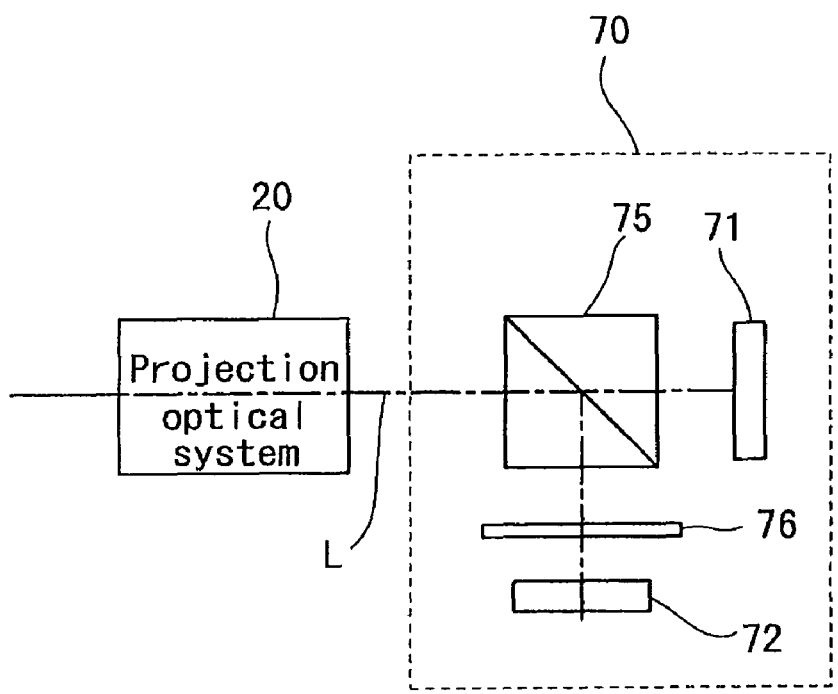
FIG. 5 is a view showing a modified embodiment of the optotype forming unit.

In addition, while the LCDs 71 and 72 have the positional relation that the LCD 71 is rotated 90 degrees with respect to the LCD 72 (conversely, the positional relation that the LCD 72 is rotated 90 degrees with respect to the LCD 71) in order to make the polarization directions of the LCDs 71 and 72 having the same characteristics perpendicular to each other as shown in FIGS. 2A and 2B in the preferred embodiment of the present invention, the present invention is not limited thereto. It is also preferable that a phase difference plate (a wavelength plate) for rotating a polarizing axis is provided and placed on at least one of a first optical path between the polarization beam combiner 75 and the LCD 71 and a second optical path between the polarization beam combiner 75 and the LCD 72, and thereby the direction of linear polarized light emitted from the LCD 71 and/or the LCD 72 can be made coincide with a polarization direction of a light bundle which the polarization beam combiner 75 transmits or reflects. For example, as shown in FIG. 5, a phase difference plate (a ½ wavelength plate) 76 for rotating a polarizing axis 90 degrees is provided and placed on the second optical path between the polarization beam combiner 75 and the LCD 72 in the optical configuration shown in FIG. 2A. By having this configuration, the linear polarized light emitted from the LCD 72 can be reflected by the polarization beam combiner 75 without having the configuration where the display screen of the LCD 72 is rotated 90 degrees (i.e., without counterchanging the rows and the columns of the display addresses). The linear polarized light emitted from the LCD 71 is transmitted without change by the polarization beam combiner 75, and is combined with the linear polarized light emitted from the LCD 72.

When the light bundle passes through the phase difference plate 76, its light quantity slightly drops. Hence, considering this drop, it is preferable that if the phase difference plate 76 is provided only on the optical path at the part of the LCD 72, the light emission quantity (intensity) of the LCD 72 is controlled to increase compared with the LCD 71 in order to make the light intensity of the optotype for a left eye and the light intensity of the optotype for a right eye equal.

If a liquid crystal display arranged to emit linear polarized light having a polarizing axis oriented in the direction of 0 or 90 degrees is used for the LCDs 71 and 72, the phase difference plates 76 are provided on the first optical path at the part of the LCD 71 and on the second optical path at the part of the LCD 72. In this case, a phase difference plate having a property of rotating a polarizing axis 45 degrees is used as the phase difference plate 76 on the first optical path, and a phase difference plate having a property of rotating a polarizing axis 45 degrees plus 90 degrees (i.e., in the opposite direction) is used as the phase difference plate 76 on the second optical path. With the use of the phase difference plates as described above, the directions of the linear polarized light emitted from the LCDs 71 and 72 can be made coincide with the directions of the polarizing axes of the polarizing plates 30L and 30R which are placed in front of the examinee's eyes, without relation to the polarization angles of the linear polarized light emitted from the LCDs 71 and 72.

In addition, in the case of using a liquid crystal display arranged to emit linear polarized light having a polarizing axis oriented in the direction of 0 or 90 degrees for the LCDs 71 and 72, it is also preferable that relative to the optical configuration shown in FIG. 2A, the LCD 71 is rotated 45 degrees and the LCD 72 is rotated 45 degrees plus 90 degrees. Alternately, it is also preferable that a polarization beam combiner having a property of transmitting linear polarized light having a polarization angle of 0 degree and reflecting linear polarized light having a polarization angle of 90 degree is used as the polarization beam combiner 75, and the LCDs 71 and 72 are integrally rotated 45 degrees together with the polarization beam combiner 75. That is, the optotype forming unit 70 is rotated 45 degrees about the optical axis L.

It is also preferable that a phase difference plate for rotating a polarizing axis 45 degrees is provided and placed on the optical paths combined by the polarization beam combiner 75. Alternately, it is also preferable that an optical system arranged to rotate an image of an optotype light bundle 45 degrees such as an image rotator is additionally provided and placed on the optical paths combined by the polarization beam combiner 75.

Figure 6A:
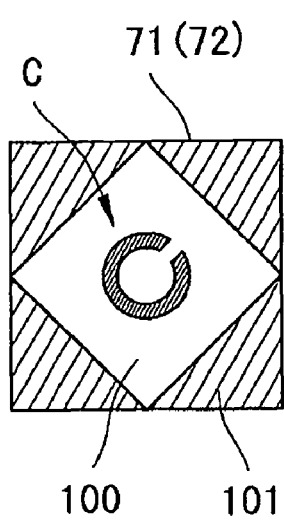
FIG. 6A is a view showing display of a test region in a case where an LCD is rotated 45 degrees, and application of a mask.
Figure 6B:
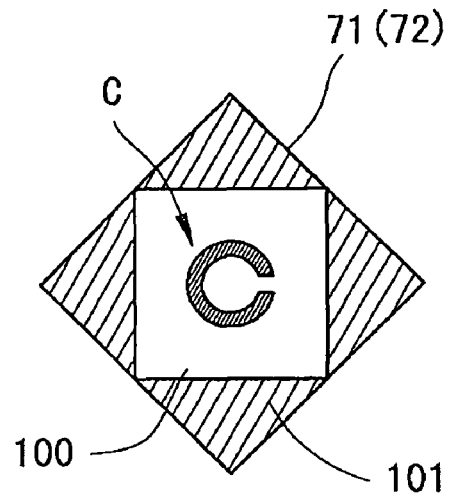
FIG. 6B is a view showing the display of the test region in a case where the LCD is rotated 45 degrees, and the application of the mask.

In the case of directly rotating the LCDs 71 and 72 45 degrees and in the case of using the optical system arranged to rotate the optotype image 45 degrees with the use of the image rotator, the display regions of the LCDs are inclined 45 degrees in the presenting window 2. In this case, application of a mask is made in order to give a square shape having horizontal sides to a test region where a background of an optotype C for a visual acuity test or other optotypes is to be displayed. To be specific, as shown in FIG. 6A, a square mask 101 is prepared which is made rotated 45 degrees with respect to the sides of the display region of the LCD 71 (or the LCD 72). The mask 101 is preferably an electronic mask made by controlling the display of the LCD, or a square mask plate placed in front of the LCD. Then, the LCDs 71 and 72 are directly or optically rotated 45 degrees, and accordingly, as shown in FIG. 6B, a test region 100 can be presented in a square shape having horizontal sides to the examinee. In displaying the optotype C for a visual acuity test such that the examinee is asked to tell the orientation, display addresses of the optotype C are controlled in accordance with the rotation angle.

While a polarization beam combiner is used to combine optotypes displayed on the first and second displays in the above-described preferred embodiment of the present invention, the present invention is not limited thereto. It is essential only that optotypes displayed on the first and second displays be combined. For example, a beam combiner is preferably used which is arranged to transmit the light bundle of the optotype displayed on the first display and reflect the light bundle of the optotype displayed on the second display, and combine the light bundles (transmission and reflection may be inverted). To be specific, a half mirror is used. In this case, the optotype light bundles from the first and second displays need to have predetermined polarizing axes. Besides, losses of light intensity are produced compared with the case of using a polarization beam combiner, so that light intensity of the first and second displays needs to be made two times as high as the optotype forming unit 70.

Figure 7:
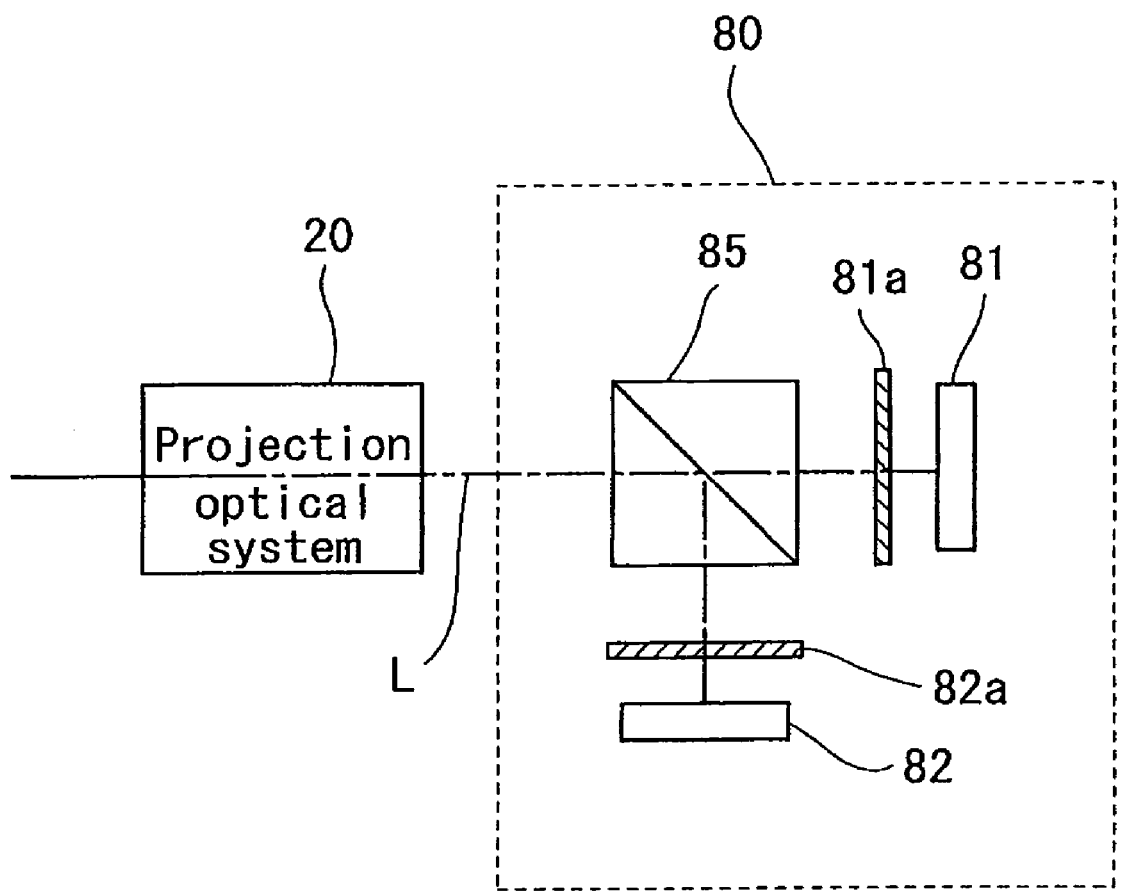
FIG. 7 is a diagram showing a configuration of an optotype forming unit which comprises two organic EL displays and a half mirror.

If the above-described display having no property of polarized light such as an organic EL display is used for the first and second displays in the configuration where the half mirror is used, the optotypes displayed on the first and second displays need to be provided with polarization directions having the above described relation. FIG. 7 is a diagram showing a configuration of an optotype forming unit 80 which comprises organic EL displays and a half mirror. Polarizing plates 81a and 82a are provided and placed between a half mirror 85 and organic EL displays 81 and 82, respectively. The polarizing plates 81a and 82a are arranged to have a relation that their polarizing axes are perpendicular to each other. For example, when the organic EL display 81 displays an optotype for a right eye, the polarizing plate 81a is placed to have the polarizing axis oriented in the direction of 135 degrees, and the polarizing plate 82*a* is placed to have the polarizing axis oriented in the direction of 45 degrees. Thus, even though the first and second displays and the beam combiner have no property of polarized light, optotype light bundles having the polarizing axes respectively for the right and left eyes can be formed in the optotype forming unit 80 with the use of the polarizing plates.

While the LCDs 71 and 72 are positioned such that the center lines C1 and C2 are combined coaxially on the optical axis L and the optotypes for right and left eyes are presented to the respective eyes in the above-described preferred embodiment of the present invention, the present invention is not limited thereto. It is essential only that the presented optotypes for right and left eyes be combined at positions of the examinee's eyes appropriately for a binocular vision test (e.g., a fusion stimulus optotype is presented at a center position (at a position of a visual axis) of each of the right and left eyes). Hence, it is essential only that the LCDs 71 and 72 be positioned such that the centers of the optotypes for right and left eyes are combined. For example, in the case of displaying the optotypes (the test regions) in portions of the display regions of the LCDs 71 and 72 and masks are applied on the other portions of the display regions, the middles of the optotypes (the test regions) are regarded as the centers.

While the configuration of the apparatus in the above-described preferred embodiment of the present invention is such that the optotype formed by the optotype forming unit 70 is projected onto the examinee's eye by the projection optical system and a virtual image of the optotype is presented to the examinee, the present invention is not limited thereto. It is also preferable to use the present invention in an optotype presenting apparatus of a projection type which comprises a projection optical system comprising a lens arranged to enlarge and project the optotype formed by the optotype forming unit 70 onto a screen which is apart at a given distance for a test, and other constituent elements.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An optotype presenting apparatus arranged to present an optotype to an examinee's eye, the apparatus comprising:
    a main body which comprises:
        an optotype forming unit comprising a first display arranged to display an optotype and a second display arranged to display an optotype, and a beam combiner arranged to combine optical paths of the first display and the second display, the optotype forming unit arranged:
            in a case where light bundles of the optotypes from the first display and the second display have polarizing axes, to adjust the polarizing axes of the optotype light bundles; and
            in a case where light bundles of the optotypes from the first display and the second display have no polarizing axis, to provide polarizing axes to the optotype light bundles by using polarizing plates,
        whereby the optotype light bundles from the beam combiner form optotypes which have the polarizing axes perpendicular to each other; and
        a projection optical system arranged to project the optotype light bundles formed by the optotype forming unit onto an examinee's eye at a given distance for a test;
    an optotype selecting unit with which optotypes for a test including a first optotype for a visual acuity test and a second optotype for a binocular vision test using polarization can be selected; and
    a display control unit arranged to control display of the first display and display of the second display based on a selection signal from the optotype selecting unit, the display control unit arranged:
        in a case where the first optotype is selected, to control one of the first display and the second display to display the first optotype; and
        in a case where the second optotype is selected, to control one of the first display and the second display to display the second optotype for a left eye and control the other one to display the second optotype for a right eye.

2. The optotype presenting apparatus according to claim 1, further comprising a memory arranged to store a mutual relation between an address of a pixel in the first display and an address of a pixel in the second display, wherein
    the display control unit is arranged, in a case where the second optotype is selected, to control, based on the stored mutual relation, the display of the first display and the display of the second display, and display the second optotype for a left eye and the second optotype for a right eye after combination by the beam combiner so as to have a predetermined positional relation.

3. The optotype presenting apparatus according to claim 1, wherein
    the first display and the second display are liquid crystal displays of the same type which are each arranged to emit a light bundle having a polarizing axis oriented in a predetermined direction, and the first display and the second display are positioned to have a positional relation such that one of the first display and the second display is rotated 90 degrees with respect to the other one, and
    the display control unit is arranged, in a case where the second optotype is selected, to control, based on the positional relation between the first display and the second display, the display of the first display and the display of the second display, and display the second optotype for a left eye and the second optotype for a right eye after combination by the beam combiner so as to have a predetermined positional relation.

4. The optotype presenting apparatus according to claim 3, wherein
    the beam combiner is a polarization beam combiner having a property of transmitting a light bundle which has a first polarizing axis and reflecting a light bundle which has a second polarizing axis perpendicular to the first polarizing axis, and
    the polarizing axis of the light bundle from one of the first display and the second display is made to coincide with the first polarizing axis, and the polarizing axis of the light bundle from the other one is made to coincide with the second polarizing axis.

5. The optotype presenting apparatus according to claim 3, wherein the beam combiner is a half mirror.

6. The optotype presenting apparatus according to claim 1, wherein
the first display and the second display are liquid crystal displays of the same type which are each arranged to emit a light bundle having a polarizing axis oriented in a predetermined direction,
the optotype forming unit further comprises a phase difference plate arranged to rotate a polarizing axis of a light bundle 90 degrees, which is placed on one of an optical path between the first display and the beam combiner and an optical path between the second display and the beam combiner, and
the display control unit is arranged, in a case where the second optotype is selected, to control, based on a positional relation of the polarizing axis of the light bundle rotated by the phase difference plate, the display of the first display and the display of the second display, and display the optotype for a left eye and the optotype for a right eye after combination by the beam combiner so as to have a predetermined positional relation.

7. The optotype presenting apparatus according to claim 6, wherein
the beam combiner is a polarization beam combiner having a property of transmitting a light bundle which has a first polarizing axis and reflecting a light bundle which has a second polarizing axis perpendicular to the first polarizing axis, and
the polarizing axis of the light bundle from one of the first display and the second display is made to coincide with the first polarizing axis, and the polarizing axis of the light bundle from the other one is rotated by the phase difference plate and is made to coincide with the second polarizing axis.

8. The optotype presenting apparatus according to claim 6, wherein the beam combiner is a half mirror.

9. The optotype presenting apparatus according to claim 1, wherein
the first display and the second display are displays of the same type which are each arranged to emit a light bundle having no polarizing axis, and
the beam combiner is a polarization beam combiner having a property of a polarizing plate, that is a property of transmitting a light bundle which has a first polarizing axis and reflecting a light bundle which has a second polarizing axis perpendicular to the first polarizing axis.

10. The optotype presenting apparatus according to claim 1, wherein
the first display and the second display are displays of the same type which are each arranged to emit a light bundle having no polarizing axis,
the beam combiner is a half mirror, and
the optotype forming unit further comprises a polarizing plate which is placed on an optical path between the first display and the beam combiner, and a polarizing plate which is placed on an optical path between the second display and the beam combiner, the polarizing plates having polarizing axes perpendicular to each other.

* * * * *